US00PP13171P2

(12) United States Plant Patent
Mowrey et al.

(10) Patent No.: US PP13,171 P2
(45) Date of Patent: Nov. 5, 2002

(54) PLUM TREE NAMED 'SUPLUMTWENTYTWO'

(75) Inventors: Bruce D. Mowrey, La Selva Beach; David W. Cain, Bakersfield, both of CA (US)

(73) Assignee: Sun World International, Inc., Bakersfield, CA (US)

( * ) Notice: Subject to any disclaimer, the term of this patent is extended or adjusted under 35 U.S.C. 154(b) by 0 days.

(21) Appl. No.: 09/793,061

(22) Filed: Feb. 26, 2001

(51) Int. Cl.[7] ..... A01H 5/00
(52) U.S. Cl. ..... Plt./184
(58) Field of Search ..... Plt./184

*Primary Examiner*—Bruce R. Campell
*Assistant Examiner*—Susan B. McCormick
(74) *Attorney, Agent, or Firm*—Knobbe, Martens, Olson & Bear, LLP

(57) ABSTRACT

A new and distinct plum variety that produces very early-ripening fruit with a mildly sweet taste. The fruit flesh is pale yellow near the pit cavity and red throughout the rest of the flesh which darkens with ripening. The fruit is not prone to fruit drop and has good keeping quality for the fresh market.

1 Drawing Sheet

LATIN NAME

*Prunus salicina.*

VARIETY

'Suplumtwentytwo.'

BACKGROUND AND SUMMARY OF THE INVENTION

This invention relates to the discovery and asexual propagation of a new variety of plum, *Prunus salicina* cv. 'Suplumtwentytwo.' The new variety was first hybridized by Bruce D. Mowrey and selected and evaluated by David W. Cain near Wasco, Kern County, Calif., the variety being originated by open pollination of an unnamed, unpatented Sun World plum selection, designated as 91P-001. The new variety is characterized by its very early-ripening fruit with a mildly sweet taste. The fruit flesh is pale yellow near the pit cavity and red throughout the rest of the flesh which darkens with ripening. The fruit is not prone to fruit drop and has good keeping quality for the fresh market.

'Suplumtwentytwo' has as its seed parent an unnamed, unpatented plum variety designated as 91P-001. The pollen parent is unknown, as the new plum variety cv. 'Suplumtwentytwo' arose from an open-pollination of the seed parent. The parent varieties were first crossed in 1993, with the date of sowing November 1993 and the first flowering being 1996. The new 'Suplumtwentytwo' varety was first asexually propagated by David W. Cain in May 1998, near Wasco, Kern County, Calif., by budding onto 'Flordaguard' rootstock.

The new variety 'Suplumtwentytwo' is distinguished from its seed parent 91P-001 by producing dark red firm flesh, in contrast to the yellow flesh of the seed parent 91P-001 which becomes red only when the fruit becomes very softly ripe. The surface of the new variety is smooth in contrast to the corrugated surface of 91P-001. 'Suplumtwentytwo' further differs from its seed parent by having slightly larger fruit, averaging about 6 cm in diameter compared with an average diameter of 5.5 cm for 91P-001. 'Suplumtwentytwo' ripens approximately 10 days before 91P-001.

The new plum variety cv 'Suplumtwentytwo' most nearly resembles the interspecific tree 'Flavorosa' variety (U.S. Plant Pat. No. 10,285). It is distinguished from 'Flavorosa' by possessing fruits having flesh that is generally more pale yellow when commercially ripe, with a lighter red coloration near the pit cavity in contrast to the darker coloration at the pit cavity of the 'Flavorosa' variety. The fruit of 'Suplumtwentytwo' hold more tenaciously to the tree and are not as prone to fruit drop as the fruit approach maturity, in comparision with the 'Flavorosa' variety. 'Suplumtwentytwo' possesses smaller size leaves having a more rounded, elliptic, and less pronounced pointed lanceolate apex as opposed to the 'Flavorosa' variety. The new variety 'Suplumtwentytwo' is further distinguished from the 'Flavorosa' in not being an interspecific hybrid having *Prunus armeniaca* in its parentage.

The new plum variety cv. 'Suplumtwentytwo' ripens at approximately the same time as 'Red Beaut' (U.S. Plant Pat. No. 2,539, expired) but differs from 'Red Beaut' by producing black-skinned fruit with red flesh and an oblate shape, as compared with the red-skinned fruit, yellow flesh, and ovate shape of the 'Red Beaut' variety.

The new plum variety cv. 'Suplumtwentytwo' variety has been shown to maintain its distinguishing characteristics through successive asexual propagations by, for example, budding.

BRIEF DESCRIPTION OF THE FIGURE

The accompanying drawing in FIG. 1 illustrates in full color.

DETAILED BOTANICAL DESCRIPTION OF THE INVENTION

Figure 1:
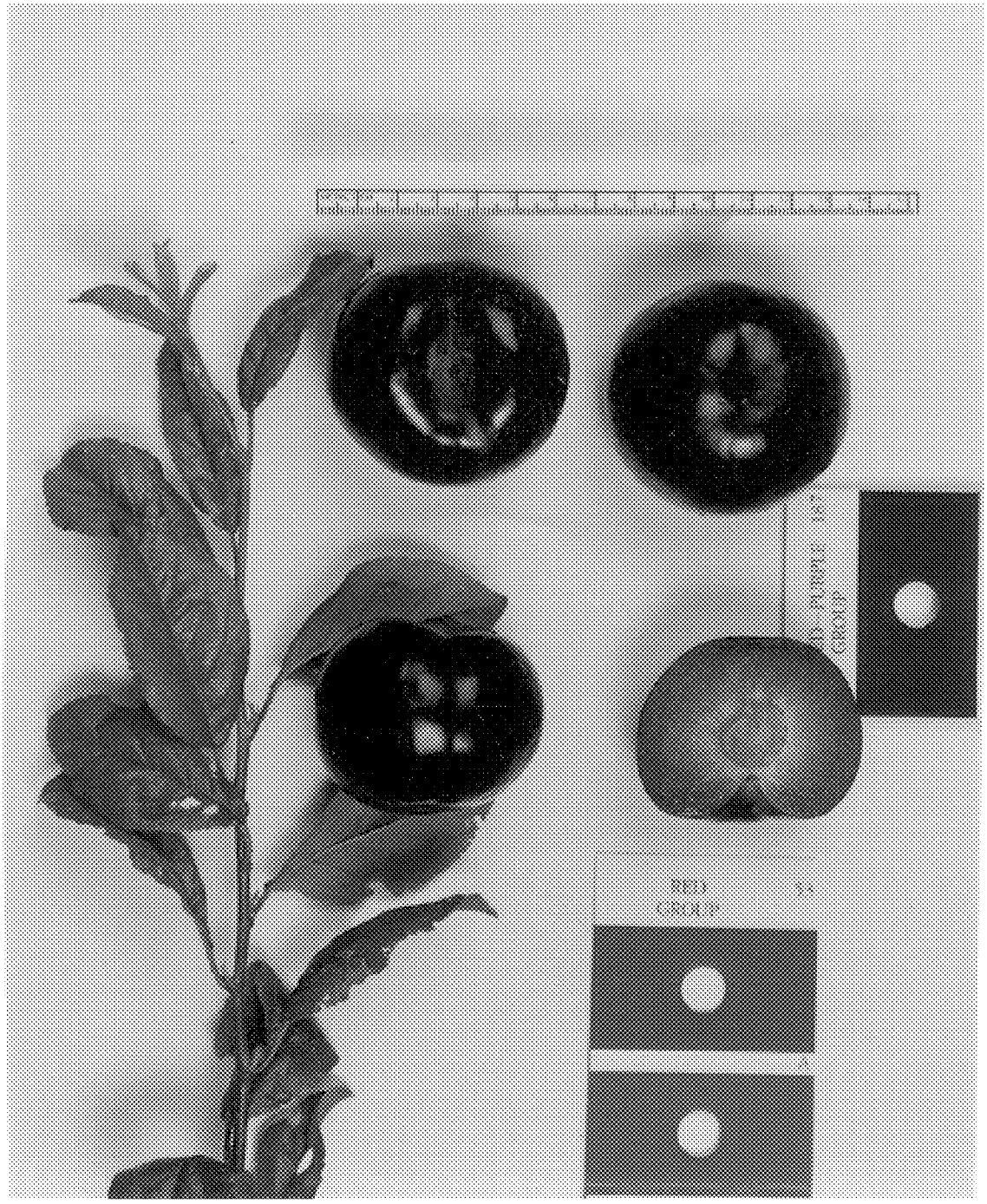

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England.

The descriptive matter which follows pertains to 8 year old 'Suplumtwentytwo' plants grown in the vicinity of Wasco, Kern County, Calif., during 2000, and is believed to apply to plants of the variety grown under similar conditions of soil and climate elsewhere:

TREE

General:
- *Height.*—Reduced by pruning to approximately 300 cm to 340 cm.
- *Width.*—Maintained by pruning to approximately 245 cm wide.
- *Growth per season.*—About 45 to 100 cm/season (affected by cultural and environmental factors).
- *Vigor.*—Medium.
- *Habit.*—Semi-upright.
- *Density of foliage.*—Medium.
- *Shape.*—Vase formed.
- *Hardiness.*—Hardy in Kern County, Calif.
- *Productivity.*—Productive.
- *Fruit bearing.*—Regular bearer.
- *Root stock.*—Flordaguard.

Trunk:
- *Shape.*—Medium.
- *Trunk diameter.*—About 20 cm at 30 cm above soil level.
- *Surface texture of bark.*—Medium shaggy (varies with age).
- *Bark color.*—About 200D (varies with age of tree).

Branches:
- *Shape.*—Round.
- *Branch diameter at 70 cm above soil line.*—About 7 cm to 9 cm.
- *Surface texture.*—Smooth to medium shaggy.
- *Surface color.*—About 166B to 200C (varies with age of tree).
- *Surface appearance.*—Semi-glossy.

Lenticels:
- *Number.*—Few.
- *Size on typical flowering shoot.*—About 0.8 mm diameter.
- *Color.*—About 156B.

LEAVES

General:
- *Average length.*—About 7.6 cm.
- *Average width.*—About 3.2 cm.
- *Size.*—Medium — small.
- *Outline.*—Elliptic.
- *Profile.*—Up folded.
- *Leaf blade tip.*—Curved downwardly.
- *Angle of tip.*—Nearly right angle.
- *Margin.*—Crenate.
- *Undulation of margin.*—Slight.
- *Apex.*—Mucronate.
- *Base.*—Cuneate.
- *Thickness.*—Medium.
- *Venation pattern.*—Pinnate.
- *Vein color.*—144B.

Upper surface:
- *Color.*—About 147A.
- *Glossiness.*—Weak.
- *Pubescence.*—Absent.
- *Surface texture.*—Smooth.
- *Surface appearance.*—Dull.

Lower surface:
- *Color.*—About 147B.
- *Glossiness.*—Weak.
- *Pubescence.*—Absent.
- *Surface textue.*—Smooth.
- *Surface appearance.*—Dull.

Petiole:
- *Length of petiole.*—Medium, about 1 cm.
- *Thickness of petioles.*—Medium, about 2 mm.
- *Petiole color.*—About 144A with highlights of red 47B.

Glands:
- *Average number.*—About 2.
- *Positioning.*—(a) On both leaf base and petiole. (b) Alternate.
- *Size.*—About 0.8 mm long and 0.8 mm wide.
- *Shape.*—Globose.
- *Color.*—Yellow-Green 147A, becoming Red-Purple 59A as they age.

Stipules:
- *Persistence.*—Persistent.

Wood (leaf) buds:
- *Shape.*—Conical.
- *Size (on a typical flowering shoot of about 5 mm diameter).*—Small, about 2 mm wide (at widest point) by about 2.5 mm long.
- *Position relative to shoot.*—Slightly — held out.
- *Support.*—Not decurrent.
- *Time of bud burst.*—About 2 days after first bloom.
- *Date of bud burst.*—Feb. 27, 2000 in growing area near Wasco, Kern County, Calif.

Flowering shoots:
- *Anthocyanin coloration.*—Absent.
- *Thickness.*—Medium, about 0.47 cm.
- *Internode length.*—Short — medium, about 1.5 cm. (on 0.47 cm diameter shoot).
- *Density of buds.*—Medium.
- *Distribution.*—Isolated in groups of 2 or more, on spurs and one year old shoots and older wood.
- *Ratio of wood (leaf) buds to flowering shoots.*—1:4 (ranges from 1:4 to 1:9).

FLOWERS

Flower-buds:
- *Hardiness.*—Hardy in Kern County, Calif.
- *Width on a typical shoot of 5 mm diameter.*—About 3 mm at widest point.
- *Length on a typical shoot of 5 mm diameter.*—About 3.5 mm.
- *Shape.*—Ovoid.
- *Positioning.*—Free.
- *Pubescence.*—Absent.
- *Color.*—About 177A.

General:
- *Date of first bloom.*—Feb. 25, 2000.
- *Date of full bloom.*—Mar. 2, 2000.
- *Time of bloom.*—Medium, as compared with similar varieties in the growing area of Wasco, Kern County, Calif.
- *Duration of bloom.*—Medium, about 10 days.
- *Size (diameter of the fully open flower).*—Medium, about 1.9 cm.
- *Shape.*—Rosaceous.

*Petals.*—Free.
*Color* (*fully opened flower*).—White.
Peduncle:
*Length.*—Short, about 0.35 cm.
*Width.*—About 0.9 mm.
*Color.*—About 145A.
*Pubescence.*—Absent.
Receptacle:
*Depth.*—Medium.
*Pubescence of inner surface* (*at white bud stage*).—Absent.
*Pubescence of outer surface.*—Absent.
Sepals:
*Size.*—About 2 mm wide by about 2.5 mm long.
*Color.*—About 145A.
*Positioning.*—Adpressed to petals.
*Shape.*—Ovate.
*Pubescence of inner surface.*—Absent.
*Pubescence of outer surface.*—Absent.
*Frequency of flowers with double sepals.*—None.
Petals:
*Frequency of flowers with double petals.*—None.
*Size.*—Medium, about 0.8 cm wide by about 1.0 cm long.
*Shape.*—Circular.
*Shape of apex.*—Rounded.
*Shape of base.*—Petal narrows as it nears base.
*Claw length.*—Short.
*Margin waviness.*—Weak.
*Base angle.*—Medium.
*Division of upper margin.*—Entire.
*Pubescence of inner surface.*—Absent.
*Pubescence of outer surface.*—Absent.
*Color* (*inner surface*).—White.
*Color* (*outer surface*).—White.
Stigma:
*Position* (*as compared with anthers*).—Level.
Anthers:
*Color* (*just before dehiscence*).—Yellow (23B) with Red (45D) shadings.
Pollen:
*Color.*—About 13A.
Stamens:
*Position.*—Perigynous.
Pistil:
*Length at full bloom.*—About 7 mm long.
*Frequency of supplementary pistils.*—Absent.
*Number.*—Always one.
Ovary:
*Diameter.*—About 0.9 mm.
*Color.*—About 143A.
*Pubescence.*—Absent.
Style:
*Shape.*—Slender.
*Color.*—About 145B.
*Pubescence* (*of base*).—Absent.

FRUIT

General:
*Maturity when described.*—Firm — ripe.
*Date.*—May 22, 2000.
*Size.*—Uniform; medium; about 5.2 cm long from stem-end to apex.
*Weight.*—About 103 g.
*Diameter in line with suture plane.*—About 6.0 cm.
*Diameter perpendicular to suture plane.*—About 6.0 cm.
*Form.*—Oblate.
*Position of maximum diameter.*—Towards middle.
*Symmetry about the suture.*—Symmetric.
*Season ripening.*—Very early.
*Use.*—Fresh market.
*Keeping quality.*—Good.
*Resistance to.*—Insects: medium (typical of Japanese plums). Diseases: medium(typical of Japanese plums).
*Shipping quality.*—Good — fruit stored for 3 weeks at 38° F.–42° F. showed no internal browning or mealiness of flesh.
Suture: An inconspicuous line extending from base to apex.
Ventral surface:
*Shape.*—Rounded, slightly lipped throughout.
*Lips.*—Nearly equal.
*Depression of apex.*—Slightly.
*Pistil base.*—Not persisting.
*Pubescence at apex.*—Absent.
Stem cavity:
*Shape.*—Rounded, but slightly elongated in suture plane.
*Depth.*—About 0.6 cm.
*Breadth.*—About 0.7 cm.
*Markings.*—None.
Base:
*Shape.*—Rounded to truncate.
Apex:
*Shape.*—Slightly rounded to truncate.
Pistil point:
*Shape.*—Oblique.
Stem:
*Length.*—About 1.5 cm, medium.
*Color.*—About 143C.
*Adherence to stone.*—Stem adheres to stone moderately but separates from the stone more easily than from the tree.
Skin:
*Thickness.*—Medium.
*Texture of skin when harvested.*—Smooth and crisp.
*Reticulation.*—Absent.
*Roughness.*—Absent.
*Taste.*—Mildly tart.
*Tenacity.*—Tenacious to flesh.
*Tendency to crack.*—None, in either wet or dry season.
*Color.*—About 187A, becoming black as it ripens.
*Down* (*pubescence*).—None.
*Bloom.*—Present.
Flesh:
*Color.*—About Grayed-Yellow 161B near stone and about Red 46B throughout the rest of the flesh. Flesh darkens to about Grayed-Purple 187CC when fully ripe.
*Amygdalin.*—Wanting.
*Juice.*—Abundant to moderate.
*Sugar content.*—Medium high (about 16.5% SS).
*Texture.*—Medium — melting.
*Amount of flesh fibers.*—Few.
*Size of flesh fibers.*—Small.
*Tenderness of flesh fibers.*—Tender.
*Ripens.*—Even.
*Flavor.*—Mildly sweet.
*Aroma.*—Distinct.
*Eating quality.*—Good.
*Stone/flesh ratio.*—1.6 g.: 105 g.

STONE

General:

*Adherence to flesh.*—Cling.
*Fibers.*—Short.
*Size.*—Small.
*Length.*—About 1.8 cm.
*Breadth.*—About 1.9 cm.
*Width of stalk end.*—About 0.2 cm.
*Angle of stalk end.*—Obtuse.
*Thickness.*—About 1.1 cm.
*Form* (*profile*).—Globose-eliptical.
*Form* (*ventral view*).—Sub-globular.
*Base.*—Nearly — straight.
*Hilum.*—Narrow.
*Apex.*—Obtuse, with a small sharp point.
*Position of maximum breadth.*—Towards stalk end.
*Sides.*—Nearly equal.
*Surface.*—Rough, but not heavily pitted or furrowed.
*Outgrowing keel.*—Well developed.
*Ridges.*—Nearly rounded.
*Pits.*—Angular.
*Ventrical edge.*—Three distinct keels running side-by-side throughout, with the central keel parallel but at a right angle to the other two.
*Dorsal edge.*—Medium width with a distinct shallow groove throughout.
*Color of stone.*—About 164C.
*Tendency to split.*—None, in either wet or dry season.
*Kernel shape.*—Oval.
*Astringency of kernel.*—Bitter.
*Viability of kernel.*—Viable.
*Length of kernel when dried.*—About 12 mm.
*Diameter of kernel in line with suture plane when dried.*—About 10 mm.
*Diameter of kernel perpendicular to suture plane when dried.*—About 5 mm.

What is claimed is:

1. A new and distinct plum tree as herein described and illustrated.

* * * * *